United States Patent [19]
Clare et al.

[11] Patent Number: 5,452,718
[45] Date of Patent: Sep. 26, 1995

[54] ELECTRODE CONSTRUCTION, ASSEMBLY THEREOF, PACKAGE THEREFOR AND METHOD

[76] Inventors: Christopher R. Clare, 12620 La Ciesta Dr., Los Altos, Calif. 94022; Albert J. Highe, 972 Emerald Hill Rd., Redwood City, Calif. 94061; Mir A. Imran, 731 Barron Ave., Palo Alto, Calif. 94306

[21] Appl. No.: 159,798

[22] Filed: Nov. 26, 1993

Related U.S. Application Data

[63] Continuation-in-part of Ser. No. 983,824, Dec. 1, 1992, Pat. No. 5,345,934, which is a continuation-in-part of Ser. No. 790,412, Nov. 8, 1991, abandoned.

[51] Int. Cl.$^6$ ........................................................ A61N 1/04
[52] U.S. Cl. .................................................. 128/639; 439/909
[58] Field of Search ...................................... 128/639, 640; 607/152, 115; 439/909, 846, 843, 859, 860

[56] References Cited

U.S. PATENT DOCUMENTS 4,706,679 11/1987 Schmidt et al. ..................... 128/639

Primary Examiner—William E. Kamm
Assistant Examiner—Scott M. Getzow
Attorney, Agent, or Firm—Flehr, Hohbach, Test, Albritton & Herbert

[57] ABSTRACT

An electrode construction comprising a support structure, a conductive electrode material carried by the support structure and having a length and a width and having proximal and distal extremities, said support structure including a compliant sleeve having an open end and surrounding the distal extremity of the conductive electrode material while permitting the conductive electrode material to protrude through the open end, and conductive contact means making contact with the proximal extremity of the conductive electrode material.

20 Claims, 2 Drawing Sheets

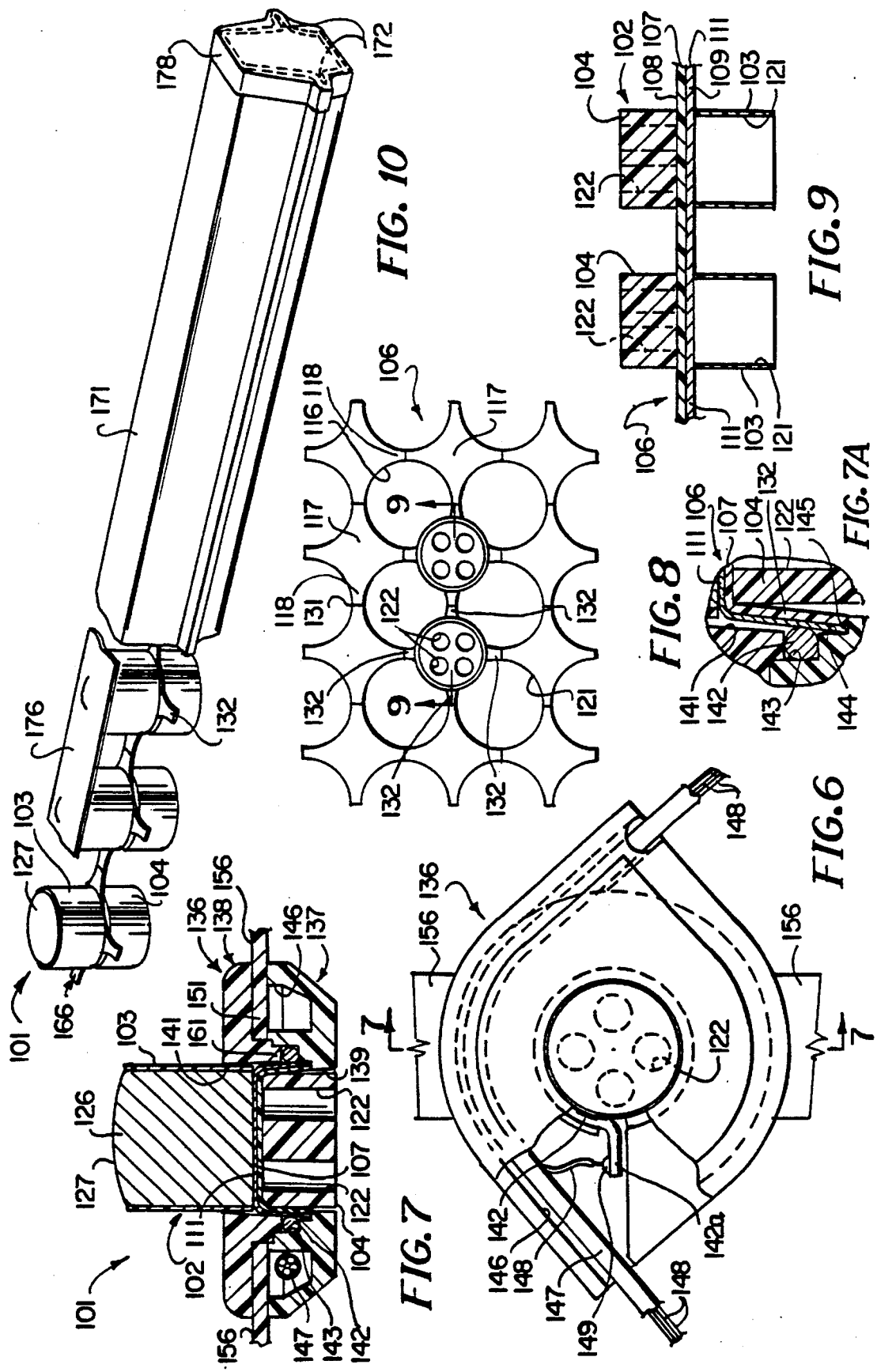

5,452,718

ELECTRODE CONSTRUCTION, ASSEMBLY THEREOF, PACKAGE THEREFOR AND METHOD

This application is a continuation-in-part of application Ser. No. 07/983,824 filed on Dec. 1, 1992, now U.S. Pat. No. 5,345,934 which is a continuation-in-part of application Ser. No. 07/790,412 filed on Nov. 8, 1991, now abandoned.

This invention relates to an electrode construction, assembly thereof, package therefor and method which is particularly useful in making EEG measurements.

Electrodes heretofore utilized for making EEG measurements typically have been of high impedance and have sought to make good contact with the skin of the patient. This has involved the use of electrodes whose area of contact is not well controlled which are based upon hydrogel kinds of materials. Such electrodes formed of hydrogel have a tendency to lose water and therefore are inappropriate for long term monitoring. Also for this reason they have a short shelf life. In addition, with respect to prior art electrodes, there has been an inability to compensate for the varying thicknesses of hair on the head of a patient when making measurements on the head. In addition, prior art electrodes typically must be prepared prior to use. Preparation of such electrodes requires considerable time and results in electrodes whose potentials which have not stabilized before use resulting in increased noise in EEG signals. There is therefore a need for a new and improved electrode construction which overcomes these disadvantages.

In general, it is the object of the present invention to provide an electrode construction which is particularly useful in making EEG measurements.

Another object of the invention is to provide an electrode construction which can utilize gel electrolytes as well as dry-type electrode materials.

Another object of the invention is to provide an electrode construction and assembly thereof that can be made inexpensively.

Another object of the invention is to provide electrode construction and assembly thereof which makes it possible to obtain reliable and good contact with the gel electrolyte.

Another object of the invention is to provide an electrode construction of the above character which can be used for long term monitoring and which has a relatively long shelf life.

Another object of the invention is to provide packaging and a method for the electrode construction of the present invention which provides electrochemically stable electrodes that are matched and do not require further conditioning before use.

Additional objects and features of the invention will appear from the following description in which the preferred embodiments are set forth in detail in conjunction with the accompanying drawings.

FIG. 6 is a top plan view with certain parts broken away of another embodiment of an electrode assembly incorporating the present invention.

FIG. 7 is a cross-sectional view taken along the line 7—7 of FIG. 6.

FIG. 7a is an enlarged portion of the cross-sectional view shown in FIG. 7.

FIG. 8 is a plan view of a substrate with a plurality of electrode assemblies formed thereon in accordance with the present invention.

FIG. 9 is a cross-sectional view taken along the line 9—9 of FIG. 8.

FIG. 10 is an isometric view of a package for a plurality of electrode assemblies of the type shown in FIG. 7.

In general, the electrode construction of the present invention consists of a support structure. A conductive material is carried by the support structure and has length and a width. The conductive material has an aspect ratio in which the length is at least as great as the width.

Figure 1:
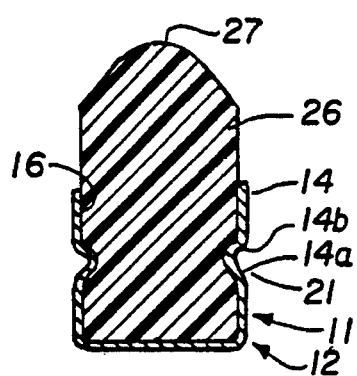
FIG. 1 is a side elevational view in cross-section of an electrode construction incorporating the present invention utilizing a dry-type conductive material.

More in particular, as shown in FIG. 1 of the drawings, the electrode construction 11 consists of a support structure in the form of a casing 12 which is formed of a conductive material. The casing 12 need not be highly conductive because it is only necessary to pass a small amount of current. Thus, it can be formed of a metal such as brass. It also can be formed of a conductive plastic or a metallized plastic. The casing 12 is shown as being generally cylindrical in shape and can be formed as a single piece deep-drawn casing. The casing 12 is provided with a circular top wall and a cylindrical sidewall 14 adjoining the top wall which defines a cylindrical recess 16 therein.

An annular recess 21 is formed in the casing 12 is adapted to be engaged by spring fingers (not shown) of the type disclosed in the co-pending application Ser. No. 07/790,412 filed on Nov. 8, 1991. The recess 21 is provided with an upwardly and inwardly inclined portion 14a as viewed in FIG. 1, and an upwardly and outwardly inclined portion 14b as shown in FIG. 1.

A conductive electrode material 26 is disposed within the recess 16 in the casing 12. The conductive material 26 can be of a self-supporting, dry-like material such as that disclosed in co-pending application Ser. No. 07/582,749 filed on Sep. 14, 1992. As described therein, that material can be in the form of a conductive elastomer which has silver-coated glass particles disposed therein. The conductive material 26 as shown in FIG. 1 is generally cylindrical in shape and extends beyond the casing 12 and has a rounded tip 27. The electrode construction 11 has an aspect ratio in which the length is at least as great as the width and as shown, has a length which is approximately the same as its width. By way of example, an electrode constructed in accordance with the present invention had a diameter of 0.3" and had a length of 0.5".

The surface forming the rounded tip 27 can be coated with a material which helps to impart electrochemical stability to the electrode material. For example, the surface of the tip which has silver-coated particles therein can be treated to form a silver silver chloride (AgCl) coating to impart electrochemical stability and to provide a reference potential. This coating can be applied by usual application. Preferably it is applied electrochemically by immersing the tip in a chloride-containing electrolyte bath and passing a small d.c. current i.e. one milliamp for approximately one minute through the electrode material with the negative voltage applied to a counter electrode in the electrolyte and the positive voltage applied to the support structure. The surface of the tip also can be coated with a hydrogel-type material to help bridge to and pre-wet the surface of the skin of the patient when making contact with the skin of the patient.

Figure 2:
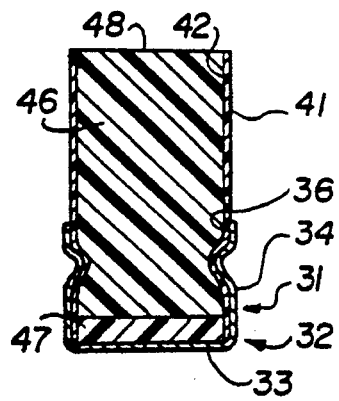
FIG. 2 is a cross-sectional view similar to FIG. 1 of another embodiment of an electrode construction incorporating the present invention utilizing a gelled electrolyte.

Another embodiment of an electrode construction incorporating the present invention is shown in the electrode construction 31 shown in FIG. 2. It consists of a support structure in the form of a cylindrical casing 32 which has a top wall 33 and a sidewall 34 with a cylindrical recess 36 therein. It is also provided with an annular recess 38 in the sidewall 34 which has generally the same conformation as the annular recess 21. A cylindrical sleeve 41 is secured to the casing 32 by suitable means as such an adhesive (not shown). The sleeve 41 is provided with a bore 42 which opens into the cylindrical recess 36 in the casing 32. The sleeve 41 can be formed of a suitable material such as plastic. The sleeve 41 can have a wall thickness ranging from a mil up to $\frac{1}{16}$". However, it should be fairly compliant so that when placed in contact with the skin of a patient it will have some "give."

The sleeve 41 should be formed of a material which substantially slows the rate of water loss and preferably is impervious to moisture and therefore serves as a moisture barrier membrane. This moisture barrier characteristic can also be achieved by applying a thin coating to the exterior of the sleeve 41. A conductive material 46 is provided within the bore 42 and extends into the cylindrical recess 36. The conductive material 46 is in contact with a coupling layer in contact with the wall 33 which provides a reference potential. It is formed of a suitable materials such as silver chloride (AgCl) deposited onto silver metal. This coating can be applied by normal application. Preferably it is applied electrochemically when the gelled electrolyte contains the coating. Preferably it is applied immersing the tip in an electrolyte or placing the tip against a suitable counter electrode and passing a small d.c. current i.e. one milliamp for approximately one minute through the electrode material with the negative voltage applied to the counter electrode and the positive voltage applied to the support structure. The conductive material 46 is provided for example, in the form of a gelled electrolyte and is retained within the sleeve 41 and provides a soft outer end 48 which can be flush with the end of the sleeve 41. It also can extend beyond the end of the sleeve. The gelled electrolyte can be rendered conductive by adding salts such as potassium chloride or sodium chloride. The gelled electrolyte can be very soft, elastomeric and tacky. The gelled electrolyte should have a cohesive strength which is greater than its adhesive strength so that when it touches the skin, it adheres to the skin but when pulled away from the skin does not fracture. In other words it will stay substantially intact. This is aided by the fact that the gelled electrolyte is retained within the sleeve 41 and adheres to the sleeve 41. It should be able to accommodate elongation, as for example have an ultimate elongation of at least 50% and preferably greater than 100%.

The material should be relatively soft and conformable having a core penetration value ranging from about 50 to about 475 ($10^{-1}$ millimeters) and preferably 50 to 300 ($10^{-1}$ millimeters) as measured by ASTM D217-88.

The conductivity of the conductive material utilized in the embodiments of the electrode construction shown in FIGS. 1 and 2 should have a conductivity at one KHz of less than 5,000 ohm-cm and preferably should have a conductivity of less than 1,000 ohm-cm.

Figure 3:
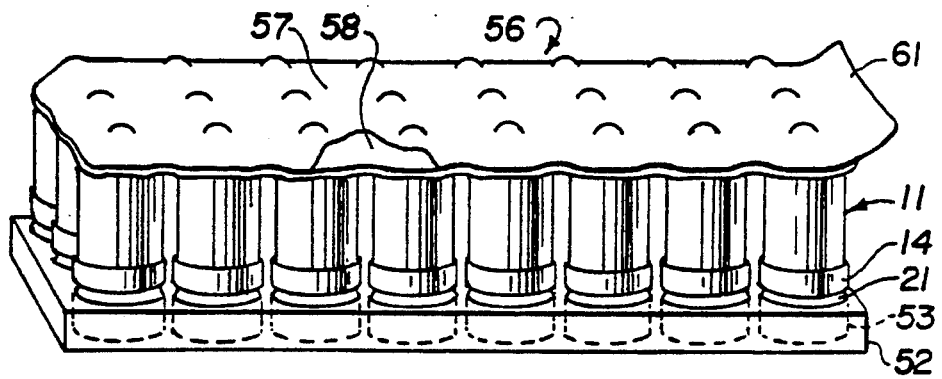
FIG. 3 is an isometric view of a package for the electrode construction shown in FIG. 2.

In the use of a conventional EEG procedure, it is typical to utilize as many as 19 electrodes in connection with a EEG headpiece of the type disclosed in co-pending application Ser. No. 07/790,412 filed on Nov. 8, 1991. Therefore, it is desirable to package at least that number in a single package or holder to minimize the differences in the reference potentials of the packaged electrodes and to stabilize the reference potentials of the electrodes. Thus, as shown in FIG. 3, there is shown holding means in the form of a holder or package 51 in which a plurality of 24 electrode constructions 11 of the type hereinbefore described are mounted therein. The holding means consists of a tray 52 which can be formed of a suitable material such as metal or a plastic coated with metal which has a plurality of holes 53 therein as for example a total of 24 holes arranged 3×8 as shown in FIG. 3. An arrangement such as 4×6 or 5×5 can be utilized if desired. The holes 53 are sized so that they can receive the casings 12 of the electrode construction 11 with the rounded ends 27 facing upwardly as shown in FIG. 3.

In order to maintain the integrity of the electrode material in the electrode constructions 11 and to minimize potential differences between electrode constructions, it is desirable to cover and bridge the Ag/AgCl coatings provided on the rounded ends 27. This is accomplished by the use of a flexible covering 56 which overlies the rounded ends 27 of the electrodes 11 and is draped into contact therewith. The covering 56 has a multilayer construction and has an outer layer 57. The outer layer 57 is a non-conductive or insulating layer and is formed of a suitable plastic or cloth. The outer layer 57 overlies an ionically conductive hydrogel layer or pad 58 which is in direct contact with the exposed surface of the rounded ends 27 of the electrodes 11. As can be seen, the covering 56 generally assumes the contours of the rounded ends and makes intimate contact with the rounded ends. The covering is provided with pull tab 61 which extends beyond the electrodes 11 and is adapted to be grasped by the hand so that the covering can be lifted off of the electrodes 11 when it is desired to utilize the same.

Figure 4:
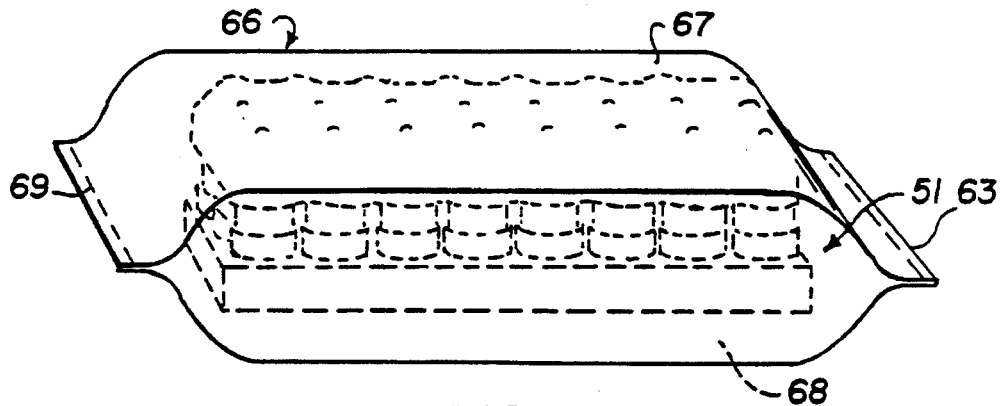
FIG. 4 is a isometric view showing an additional outer package utilized for enclosing the package shown in FIG. 3.

The holder or package 51 can be packaged in an additional hermetically sealed package, as for example a package 66 shown in FIG. 4 formed of two sheets 67 and 68 of a suitable packaging material such as a plastic material which are sealed along the edges 69 to provide a hermetically sealed package for shipping and storing the holder contained therein until it is ready to be used. Also the sheet 67 and 68 can be formed of a metallized polymer hermetically sealed to prevent water loss. When it is desired to use the same, the package can be opened by a scissors or other means to give access to the holder 51, after which the protective coating covering 56 on the holder can be removed to give access to the electrodes 11 therein. The electrodes 11 can then be utilized to make EEG measurements in the manner described in the co-pending application Ser. No. 07/790,412 filed on Nov. 8, 1991.

Similar packaging can be utilized for the electrodes 31 and consists of a holder or package 71 which is provided with a conductive tray 72 that has holes 73 therein arranged in the same manner as in the tray 52. A covering 76 of the same type as the covering 56 overlies the upper open ends of the electrodes 31 and is in contact therewith to seal and bridge the electrodes 31 until they are ready for use. The covering is provided with a pull tab 77 which is used for the same purpose as the pull tab 61. The holder 71 can then be hermetically packaged in the same manner as the holder 51.

In connection with the foregoing, it can be seen that there has been provided a new and improved electrode construction and packaging therefor. In the electrode 11 as shown in FIG. 1, the exposed surface of the rounded end serves as the reference element whereas in the electrode shown in FIG. 2, the reference element is in contact with conductor means and is buried within the gelled electrolyte. Thus in the embodiment of the electrode shown in FIG. 2, the gelled electrolyte merely forms an electrolytic bridge between the reference layer 47 and the skin of the patient engaged by the gelled electrolyte. This has an advantage in that the exposed surface 48 can be damaged without affecting the performance of the electrode.

Figure 5:
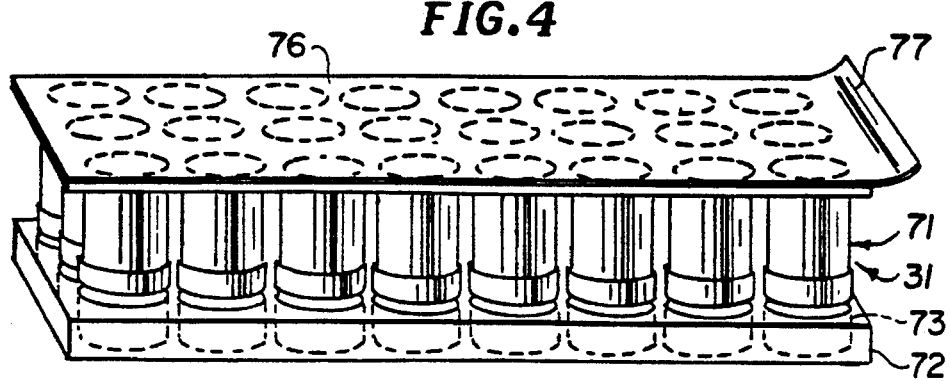
FIG. 5 is an isometric view of a package for the electrode construction shown in FIG. 2.

The packaging hereinbefore described and as shown in FIGS. 3 and 5 electrically and electrolytically interconnect all of the reference elements of the electrodes in each package. Thus, differences in reference potentials of the electrodes in any one package are minimized and remain so during storage before use. Thus, the reference potentials of the electrodes in a package are stable. The electrodes require no further conditioning and are ready to be used when removed from the package.

Another embodiment of an electrode construction and assembly thereof incorporating the present invention is shown in FIGS. 6 and 7. The electrode construction 101 consists of a support structure 102 which includes a compliant sleeve 103 and a base 104. The support structure 102 is formed by the use of a substrate 106 of the type shown in FIGS. 8 and 9.

The substrate 106 is formed of a suitable material such as a flexible sheet which carries a conductive surface at least on one side thereof. The substrate 106 can be formed of a sheet 107 of a suitable plastic as for example a polymer. The sheet 107 is provided with upper and lower surfaces 108 and 109. If the sheet 107 is formed of a non-conducting material such as a polymer, it is necessary that the sheet be provided with a conductive layer on the surface 109. This can be accomplished by depositing a conductive layer 111 on the surface 109 which can be accomplished by plating of a conductive material such as silver silver chloride or alternatively by coating the surface 109 with such a conductive layer 111. This conductive layer can also be applied in numerous ways as for example by printing the silver silver chloride on the surface in the form of silver silver chloride ink. Silver silver chloride has been selected as the conductive material because it is particularly suitable for making contact with the electrode material hereinafter described for use in the electrode construction 101 because it will resist reacting with the salts and water in the gel. The conductive layer also must be capable of making low-resistance low-noise contact as hereinafter described.

The polymer sheet 107 with the conductive layer 111 thereon can then be formed with a plurality of spaced apart circular holes 116 with each four adjacent holes being disposed in a rectangle and forming a circumscribed central area at region 117 and transversely extending areas 118 extending between the cutouts or holes 11 which carry the conductive layer 111. It should be appreciated that, if desired, the holes 116 can be provided before or after the conductive layer 111 has been applied. Such holes 116 can typically be formed in a conventional die stamping operation.

Support structures 102 are then molded over the regions 117 as shown in FIG. 8 in a compliant mass to form the base 104 on the surface 108 of the sheet 107 and the sleeve 103 on the conductive layer 111. The sleeve 103 is formed to provide a cylindrical recess 121 therein. The cylindrical recess 121 which is formed can have suitable dimensions as for example a diameter of approximately 0.3" and a depth of 0.025". The outer surface of the sleeve 103 is smooth with the distal extremity being in the form of a circle lying in a plane at right angles to the axis of the cylindrical recess 121. As shown, to reduce the amount of material utilized in the base 104, a plurality of holes 116 as for example four holes, can be formed in the base 104 (see FIG. 8). Although only two of the support structures 102 are shown in FIG. 8, it should be appreciated that each of the regions 117 typically is provided with one of the support structures 102 to thereby make possible mass production of the electrode construction 101.

The support structures 102 are formed of a suitable elastomeric material, such as Kraton G, which is a thermoplastic elastomer of a styrene-ethylene/butylene-styrene composition. It is a desirable material because it can be injection molded at a relatively low temperature, i.e. temperatures low enough so that it will not damage the plastic substrate 106 on which it is being molded. For example it can be molded at a temperature of approximately 400° F. Even at such a temperature, the mold can be kept relatively cool, as for example 150° F. so that it does not disturb the plastic material. Kraton G is a very desirable material as it has a very stable, elastic, rubbery characteristic that can be utilized for retaining the hydrogel and also to make possible a comfortable skin contact when in use. Kraton G has a durometer of 29 to 90 and preferably approximately 35, which makes it easy for the material to conform to the skin.

A conventional hydrogel material 126 is placed in the cylindrical recess 121 and is cured therein. The cylindrical recess 121 formed in the compliant sleeve 103 is slightly overfilled so that the outer or distal extremity of the hydrogel material has a rounded surface 127. The sleeve 103 serves as a good barrier and prevents air from entering through it and coming into contact with the hydrogel material.

After the support structures 102 have been molded on the substrate 106 and have been filled with cured hydrogel material 131, the support structures can be separated from each other by making die cuts along lines 131 shown in FIG. 8 so that each of the support structures 102 is provided with four conductive tangs or tabs 132 extending transversely therefrom and spaced 90 degrees apart circumferentially. Thus, as shown, each of the support structures 102 is provided with four conductive tabs 132 which have the conductive layer 111 thereon which extends into the cylindrical recesses 121. The hydrogel material 126 in the recess 121 makes intimate electrical contact with the conductive layer 111 so that the hydrogel material 126 is in electrical contact with the tabs 132. The electrode construction 101 is adapted to be mounted in a socket assembly 136 as shown in FIGS. 6 and 7.

The socket assembly 136 consists of upper and lower or first and second parts 137 and 138. The upper and lower parts 137 and 138 are formed of a suitable material such as a molded plastic. The upper and lower parts 137 and 138 are provided with axially aligned bores 139 and 141 which are adapted to receive the electrode construction 101 as hereinafter described. A conductive ring 142 formed of a suitable material such as copper coated with silver is disposed in an annular recess 143 provided in the upper part 137. The recess 143 opens into a smaller diameter recess 144 to provide a shoulder 145 which is utilized as hereinafter described. The surface defining the bore 141 of the lower part 138 has a portion thereof enclosed outwardly towards the groove 143 when the lower part 138 is mated with the top part 137. The conductive ring 142 is provided with an outwardly extending tab 142a which extends into an arcuate groove 146 in the upper part 137. As shown in FIG. 6, the arcuate groove 146 extends through approximately 180 degrees. It is adapted to receive a multi-conductor cable 147 which has a plurality of insulated conductors 148 therein, one of the insulated conductors 148 being connected to the tab 142a of the conductive ring 142 by suitable means such as solder 149. Thus as shown in FIG. 6 by way of example there could be two conductors 148 in the cable 147 entering on one side of the socket assembly 136 and three conductors 148 exiting from the other side of the socket assembly 136 because of the additional conductor making connection made to the ring 142. The conductive ring 142 is sized with respect to annular groove 143 so that its inner margin extends inwardly from the groove 143 into the groove 144 to facilitate the tabs 126 carried by the support structure 102 coming into contact therewith as hereinafter described.

The lower part 138 mates with the upper part 137 and is provided with an annular recess 151 which is adapted to receive therein strips 156 of an elastic material of the type utilized in the EEG head piece disclosed in co-pending application Ser. No. 07/790,412 filed on Nov. 8, 1991. The lower part 138 is provided with an upstanding annular shoulder 161 which is adapted to firmly engage the conductive ring 142 to retain the same within the annular recess 143. The upper and lower parts 137 and 138 can be fastened together in a suitable manner such as by pins (not shown) extending therethrough or alternatively by an adhesive.

The electrode construction 101 hereinbefore described can be packaged in a manner similar to that hereinbefore described. For example, the substrate 106 with the support structures 102 molded thereon and after they have been filled with the hydrogel material 131 can be cut into elongate strips 166 carrying a plurality of aligned electrode constructions 101. By way of example, the strips 166 can be provided with eight of such electrode constructions 101. An elongate cartridge 171 formed of a suitable material such as plastic having a generally rectangular cross-section (see FIG. 10) which is provided with two parallel longitudinally extending slots 172 therein which are adapted to receive the side margins of the strip 166 to support the electrode constructions 101 so that the upper and lower extremities of the same are out of contact with the interior of the cartridge 171.

A conductive strip 176 in the form of an ionically conductive pad of the type hereinbefore described can be placed over the hydrogel inserts 126 and if desired be provided with a release liner (not shown) that serves to act as a conductor so that all of the rounded surfaces 127 of the hydrogel inserts 126 are tied together and also are encapsulated to prevent air from coming into contact with the rounded surfaces 127. The backsides of the inserts 126 are tied together by the conductive layer 111 provided on the sheet 107 of the substrate 106.

After the strip 166 has been inserted into the cartridge 171 with the conductive strip 176 thereon, the ends of the cartridge 171 can be hermetically sealed in a suitable manner as for example by a sealing tape 178 provided on opposite ends of the cartridge to provide an airtight hermetically sealed package for the electrode constructions 101 disposed therein.

When it is desired to utilize the electrode constructions 101 for EEG measurements on a patient, the strip 166 can be removed from the cartridge 171 and the electrode constructions 101 removed therefrom by punching them out of the strip 166. The bases 104 of the electrode constructions 101 are grasped by the hand and inserted through the socket assemblies 136 by inserting the same through the top parts 137 of the socket assemblies 136 and then pressing it downwardly through the bores 139 and 141. As the electrode constructions 101 are pushed inwardly, the tabs 132 carried thereby are deflected inwardly toward the base 104 so that they extend in a direction generally parallel to the sleeve 103 with the outer conductive layer 111 facing outwardly and resiliently engaging the conductive ring 142 when they clear the annular surface defining the bore 139 in the manner shown in FIGS. 7 and 7A to ensure that excellent electrical contact is made with the conductive ring and with the hydrogel insert 126 provided in the sleeve 103. Since tabs 132 are very flexible, there is no danger of breaking of the same during insertion of an electrode constructions 101 into the socket assemblies 136. The tabs 132 engage the annular shoulder 145 which ensure that the electrode constructions 101 can only be advanced in one direction and are retained in a desired position in the socket assembly 136.

After all of the electrode constructions 101 have been inserted into the socket assembly and the appropriate EEG measurements made, the electrode constructions 101 can be readily removed from the socket assemblies by pushing them inwardly through the bores 139 and 141 in the same direction they were inserted until they clear the bores. Thereafter, they can be disposed of. Additional electrode constructions 101 can be provided in the socket assemblies 136 when desired.

It can be seen that there has been provided an electrode construction 101 which is easily made and which is very inexpensive. It is also made in such a manner so that it can be readily stored and have a relatively long shelf life.

What is claimed is:

1. An electrode construction comprising a support structure, a conductive electrode material carried by the support structure and having a length and a width and having proximal and distal extremities, said support structure including a compliant sleeve having an open end and surrounding the distal extremity of the conductive electrode material while permitting the conductive electrode material to protrude through the open end, and conductive contact means making contact with the proximal extremity of the conductive electrode material, said support structure including a flexible substrate having first and second surfaces, said substrate being formed of at least a layer of conductive material for providing said second surface, said compliant sleeve being adherent to the second surface of said substrate, said sleeve having a recess therein which extends from the open end to said second surface, said conductive material being disposed in the said recess and serving as said second surface.

2. An electrode construction as in claim 1 wherein said substrate is provided with at least one tab extending outwardly from the sleeve and being accessible from the exterior of the sleeve.

3. An electrode construction as in claim 2 wherein said substrate includes a layer of conductive material.

4. An electrode construction as in claim 2 wherein said at least one tab is formed of a material permitting the tab to be bent at a substantially right angle.

5. An electrode construction of claim 1 wherein four tabs are provided that are spaced apart circumferentially by 90°.

6. An electrode construction as in claim 1 wherein said support structure includes a base being disposed adjacent to the first surface of the substrate.

7. An electrode construction as in claim 6 wherein said base and sleeve are formed of the same material.

8. An electrode construction as in claim 7 wherein said base and sleeve are formed of a thermoplastic elastomeric composition.

9. A socket assembly for use with a cylindrical electrode construction having flexible extending tabs extending outwardly therefrom, first and second mating parts formed of an insulating material and having aligned bores extending therethrough adapted to receive the electrode construction, a conductive ring carried by the first and second parts and circumscribing at least one of the bores in the first and second parts, a conductive cable extending through the first and second parts and having a plurality of conductors and means forming a connection between one of said conductors and said conductive ring.

10. A socket assembly as in claim 9 together with a strip of elastic material secured between the first and second parts.

11. A combination of a socket assembly and an electrode construction, the socket assembly comprising first and second mating parts having aligned bores extending therethrough, a conductive ring carried by the first and second parts and being circumferentially disposed about at least one of the bores and being accessible from the aligned bores, a cable extending into the socket assembly having at least one conductor and means for connecting said at least one conductor to said conductive ring, said electrode construction comprising a flexible substrate having first and second surfaces and being formed of at least a layer of conductive material providing said second surface, a support structure carried by said flexible surface substrate, said support structure being formed of an insulating material and providing a compliant sleeve having an open end with a recess extending form the open end to the layer of conductive material, a conductive electrode material disposed within the recess and making contact with the layer of conductive material and being accessible from the open end of the sleeve, said substrate having at least one tab extending outwardly from the sleeve, said electrode construction being slidably mounted in said aligned bores and said at least one tab being bent in a direction so that it extends generally parallel to the sleeve and makes contact with the conductive ring in the socket assembly.

12. A combination as in claim 11 together with an elastic strip disposed between the first and second parts.

13. An electrode construction assembly comprising a flexible substrate having first and second surfaces, said substrate being formed of at least a layer of conductive material providing said second surface, a plurality of cut-outs provided in said substrate, said cut-outs being formed so that there is provided a substantially circumscribed central area with transversely extending areas extending between the cut-outs and being in communication with the central area, a compliant body of material bonded to the first and second surfaces overlying and underlying each circumscribed area but being free of the outwardly extending portions, a recess formed in each compliant body and serving to provide a compliant sleeve having an open end, conductive electrode material disposed in the recesses in the compliant sleeves and making contact with the conductive layer and extending through the open ends of the sleeves.

14. An assembly as in claim 13 wherein said flexible substrate is in the form of an elongate strip and wherein said compliant masses are disposed longitudinally of the strip.

15. In a method for manufacturing an electrode construction assembly, providing a flexible substrate having first and second surfaces with the substrate being formed of at least a layer of conductive material for providing the second surface, forming a plurality of sets of cut-outs in the substrate with each of the set of cut-outs providing a circumscribed central area at least one transversely extending area extending between the cut-outs, forming a body of compliant material on the first and second surfaces overlying and underlying the circumscribed area but being free of the at least one transversely extending area, forming a recess in the compliant body which opens to the conductive layer to provide a compliant sleeve having an open end, filling the recesses with a conductive electrode material so that it makes contact with the layer of conductive material and extends out of the open end of the sleeve.

16. A method as in claim 15 together with the step of separating the compliant mass from the flexible substrate at the cut-outs so that there remains the transversely extending area to provide a tab extending from the compliant mass.

17. A method as in claim 15 together with the step of cutting the flexible substrate into strips with each of the strips having a plurality of the compliant mass thereon.

18. A package comprising a plurality of electrode constructions, each electrode construction comprising a flexible substrate having first and second surfaces, said substrate being formed of at least a layer of conductive material providing said second surface, a support structure mounted on the substrate and providing a compliant sleeve having an open end, a conductive electrode material disposed in the sleeve and protruding through the open end of the sleeve and in contact with the layer of conductive material providing said second surface and an openable enclosure having an interior enclosing said plurality of electrode constructions and engaging the substrates of the electrode constructions to support the electrode construction so that the conductive electrode material of the electrode construction is out of contact with the interior of the enclosure.

19. A package as in claim 18 wherein said substrate includes outwardly extending tabs and wherein said means engaging the substrate to support the electrode constructions includes means for supporting said outwardly extending tabs.

20. A combination of a socket assembly and an electrode construction, the socket assembly comprising first and second mating parts having first and second aligned bores extending therethrough, said first part having an annular recess therein opening into said first bore and providing an annular shoulder, a conductive ring carried by the first and second parts and circumferentially disposed about the first bore and opening into the annular recess and being accessible through the annular recess, a cable extending into the socket assembly having at least one conductor and means for connecting said at least one conductor to said conductive ring, said electrode construction comprising a flexible substrate having first and second surfaces and being formed of at least a layer of conductive material providing said second surface, a support structure carried by said flexible substrate, said support structure being formed of an insulating material and providing a compliant sleeve having an open end with a recess extending from the open end to the layer of conductive material, a conductive electrode material disposed within the recess and making contact with the layer of conductive material and being accessible from the open end of the sleeve, said substrate having at least two tabs extending outwardly and radially of the sleeve, said electrode construction being slidably mounted in a forward direction through the first bore and into the second bore so that said at least two tabs are bent in a direction away from and generally parallel to the sleeve with the distal extremities of the tabs being disposed in the annular recess and engaging the annular shoulder so that the electrode construction is retained in a position in the socket assembly so that it can only move in a forward direction and cannot move in a rearward direction.

\* \* \* \* \*